United States Patent [19]

Fisher et al.

[11] 4,341,766

[45] Jul. 27, 1982

[54] DEACTIVATION OF ANTIBIOTIC-HYDROLYZING ENZYMES

[75] Inventors: Jed F. Fisher, Somerville; Jeremy R. Knowles, Cambridge, both of Mass.

[73] Assignee: Harvard College, Cambridge, Mass.

[21] Appl. No.: 163,524

[22] Filed: Jun. 27, 1980

Related U.S. Application Data

[63] Continuation of Ser. No. 26,456, Apr. 2, 1979, abandoned.

[51] Int. Cl.³ .................... A61K 35/00; A61K 31/43
[52] U.S. Cl. .................................... 424/114; 424/271
[58] Field of Search ............................. 424/114, 271

[56] References Cited

PUBLICATIONS

Johnson et al., J. Org. Chem., vol. 28, p. 1927 (1963).
Schragr, Antibiotiki, vol. 17, pp. 461–464 (1972), (Chemical Abstracts 77:56599E).
English et al., Antimicro. Agents Chemother, vol. 14, pp. 414–419 (1978).
Cartwright et al., Nature (London) vol. 278, pp. 360–361 (1979).
Doyle et al. (12/23/61), Nature, p. 1183.
Richards et al. (7/27/63), Nature, p. 354.

Primary Examiner—Jerome D. Goldberg

[57] ABSTRACT

Method and compositions for deactivating bacterial hydrolytic enzymes which attack β-lactam antibiotics.

1 Claim, 4 Drawing Figures

DEACTIVATION OF ANTIBIOTIC-HYDROLYZING ENZYMES

This is a continuation of application Ser. No. 026,456, filed Apr. 2, 1979, now abandoned.

The invention described herein was made in the course of work under a grant from the Department of Health, Education and Welfare.

This invention relates to administering chemical compounds which act synergistically with antibiotics by deactivating bacterial enzymes which normally destroy the antibiotics.

The resistance of certain bacteria to the β-lactam antibiotics such as the penicillins and cephalosporins is frequently due to β-lactamases, bacterial enzymes which catalyze the rapid hydrolysis of the β-lactam ring of the antibiotics.

One approach to the problem of overcoming the resistance of such bacteria has been the use of antibiotics which, because of their structure, are poor substrates for the hydrolytic bacterial enzymes. The cephamycins, disclosed in Nagarajan et al. (1971), J. Am. Chem. Soc., 93:2308–2310, are such hydrolysis-resistant antibiotics.

Another approach has been to use a β-lactamase deactivator which is itself not an effective antibiotic, in conjunction with an antibiotic to protect the antibiotic from hydrolysis. One such deactivator is clavulanic acid, disclosed in Howarth et al. (1976), J. Chem. Soc. Chem. Commun., 276–277; Reading et al. (1977), Antimicrob. Agents Chemother., 11:952–857; and Dumon et al. (1979), Antimicrob. Agents Chemother, 15:315–317. Other compounds which deactivate bacterial hydrolytic enzymes ae some carba-penam compounds; for example. PS-5, disclosed in Okamura et al. (1978), J. Antibiotics, 31:480–482; and olivanic acid derivatives, disclosed in Brown et al. (1977), J. Chem. Soc. Chem. Commun., 953–954 and Maeda et al. (1977), J. Antibiotics, 30:770–773. Clavulanic acid and the carba-penams are all isolated from natural sources.

Synthetic compounds have also been used to deactivate β-lactamases. Examples of 6 β-bromo-des aminopenicillanic acid, disclosed in Pratt et al. (1978), Proc. Natl. Acad. Sci. U.S.A., 75:4145–4149 and Knott-Hunziker et al. (1979), Biochem. J., 177:365–367; and 6-des-aminopenicillanic acid sulfone (CP-45, 899), disclosed in English et al. (1978), Antimicrob. Agents Chemother., 14:414–419; Pfizer Belgian Patent No. 867,859; and 6-chloro-des-aminopenicillanic acid sulfone, disclosed in Cartwright et al. (1979), Nature, 278:360–361.

One of the compounds used in the present invention, methicillin sulfone, is disclosed in Johnson et al. (1963), J. Org. Chem., 28:1927, though no usefulness is ascribed to it therein.

The method and composition of the present invention can be applied to any animal, including a human, with a bacterial infection. An N-acyl derivative of 6-aminopenicillanic acid sulfone wherein the rate constant ($k_{cat}$) in seconds$^{-1}$ of the corresponding N-acyl derivative of 6-aminopenicillanic acid is less than or equal to 100, preferably less than or equal to 25, is administered either by itself, if the patient is being treated with a β-lactam antibiotic, or in a mixture with a β-lactam antibiotic and/or, if desired, a suitable pharmaceutically acceptable non-toxic carrier substance. The relative proportions of sulfone: antibiotic administered to the patient or present in the mixture may vary from about 1:100 to 100:1 by weight, depending on specific circumstances. The dosage consequently can vary over a wide range depending upon the dosage of the desired β-lactam antibiotic, which conventionally ranges from 50 mg to 1g/kg body weight. Administration can be oral, intravenous, intramuscular, intraperitoneal, or by any other medically recognized method. When administered with a carrier, an effective amount of the active agent should be present in the carrier to provide the desired dosage.

We have discovered that in the case of certain β-lactamase deactivators, including CP-45, 899 and the compounds used in the present invention, intermediates are formed after administration which are covalently attached to the lactamases. We believe the acyl-enzyme intermediates either deacylate (resulting in the undesirable restoration of the lactamase) or fragment (resulting in the desirable deactivation of the lactamase). Since fragmentation occurs in competition with deacylation, the number of fragmentations, and hence the compound's effectiveness, can be increased by increasing the life span of the acyl-enzyme intermediates. This can be achieved by employing an N-acyl derivative of 6-aminopenicillanic acid sulfone in which the corresponding N-acyl derivative of 6-aminopenicillanic acid is a very poor substrate for β-lactamase. Since the rate constant ($k_{cat}$) of an N-acyl derivative of 6-aminopenicillanic acid is a measure of its ability to act as a substrate, this constant provides the basis for defining the class of sulfones used in the invention.

Figure 1:
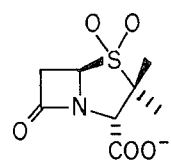
FIG. 1 shows the structure of CP-45, 899, disclosed in Pfizer Belgian Pat. No. 867,859.
Figure 2:
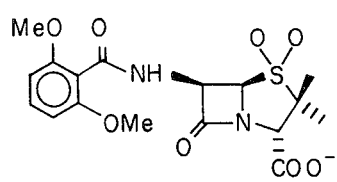
FIG. 2 shows the structure of methicillin sulfone.
Figure 3:
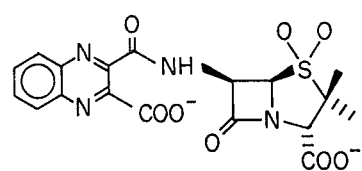
FIG. 3 shows the structure of quinacillin sulfone.
Figure 4:
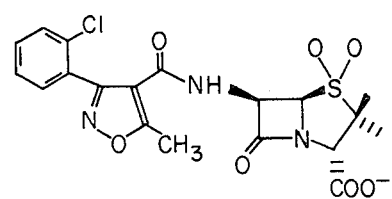
FIG. 4 shows the structure of cloxacillin sulfone.

The following specific example is intended to illustrate more fully the nature of the present invention without acting as a limitation upon its scope.

The N-acyl derivatives of 6-aminopenicillanic acid sulfone are synthesized by oxidizing the appropriate N-acyl derivative of 6-aminopenicillanic acid with aqueous permanganate, according to the procedure described in Johnson et al. (1963), J. Org. Chem. 28:1927. For example, quinacillin sulfone, a preferred embodiment of the invention, is prepared by oxidizing quinacillin with aqueous permanganate.

Table I below shows the comparative efficacies of CP-45, 899, methicillin sulfone, quinacillin sulfone, and cloxacillin sulfone, based on in vitro treatment of E. coli RTEM β-lactamase. The table shows that quinacillin sulfone is the most effective of the four compounds listed and also that the corresponding N-acyl derivative of 6-aminopenicillanic acid (i.e., quinacillin itself) has the lowest $k_{cat}$ value, which indicates poor substrate capability. Quinacillin sulfone's effectiveness is shown both by the low inactivation time, and by the low number of turnovers before inactivation (the low number of molecules of quinacillin sulfone needed to inactivate one β-lactamase molecule). Table I shows that methicillin sulfone and cloxacillin sulfone are also effective deactivating agents, though less effective than quinacillin sulfone.

TABLE I

| compound | $k_{cat}$ of corresponding N-acyl derivative of 6-aminopenicillanic acid (s$^{-1}$) | t$_{\frac{1}{2}}$ for deactivation (min) | turnovers before deactivation |
| --- | --- | --- | --- |
| CP-45, 899 | 40 | 44 | 4,500 |
| methicillin sulfone | 10 | ~1 | 22,500 |
| quinacillin | 7 | ~1 | 400 |
| sulfone cloxacillin sulfone | 24 | 1.5 | 17,000 |

What is claimed is:

1. A therapeutic mixture comprising penicillin and quinacillin sulfone in relative amounts from 1:100 to 100:1 by weight.

* * * * *